United States Patent
Winn

(10) Patent No.: US 12,133,907 B2
(45) Date of Patent: Nov. 5, 2024

(54) LIPOPHILIC THIRD GENERATION RETINOID

(71) Applicant: Actera Ingredients, Inc., Newtown, PA (US)

(72) Inventor: Daniel Winn, Kingston, NJ (US)

(73) Assignee: Actera Ingredients, Inc., Newtown, PA (US)

( * ) Notice: Subject to any disclaimer, the term of this patent is extended or adjusted under 35 U.S.C. 154(b) by 162 days.

(21) Appl. No.: 17/570,851

(22) Filed: Jan. 7, 2022

(65) Prior Publication Data

US 2022/0211597 A1    Jul. 7, 2022

Related U.S. Application Data

(60) Provisional application No. 63/134,772, filed on Jan. 7, 2021.

(51) Int. Cl.
| | |
|---|---|
| *A61K 8/37* | (2006.01) |
| *A61K 8/31* | (2006.01) |
| *A61Q 19/08* | (2006.01) |
| *C07C 69/76* | (2006.01) |

(52) U.S. Cl.
CPC .................. *A61K 8/37* (2013.01); *A61K 8/31* (2013.01); *A61Q 19/08* (2013.01); *C07C 69/76* (2013.01); *A61K 2800/30* (2013.01)

(58) Field of Classification Search
None
See application file for complete search history.

(56) References Cited

U.S. PATENT DOCUMENTS

| | | | |
|---|---|---|---|
| 8,030,352 B2 * | 10/2011 | Bosley | ................. C07C 403/20 554/224 |
| 8,404,220 B2 | 3/2013 | Ebel et al. | |
| 8,716,341 B2 | 5/2014 | Doutremepuich | |
| 9,271,930 B2 | 3/2016 | At | |
| 10,702,466 B2 | 7/2020 | Mallard et al. | |
| 2005/0163731 A1 * | 7/2005 | Pelisson | ................. A61K 8/368 424/59 |

FOREIGN PATENT DOCUMENTS

WO    WO 2019/190436    * 10/2019

OTHER PUBLICATIONS

CAS RN 106685-40-9 (entered into STN on Feb. 21, 1987) (Year: 1987).*
Dunlap et al.(British J of Dermatology 139(Suppl. 52):23-25, 1998) (Year: 1998).*
CAS RN 2392032-48-1 (entered into STN on Dec. 16, 2019) (Year: 2019).*
Pu et al.(ACS Catal 6:6692-6698, 2016) (Year: 2016).*

* cited by examiner

*Primary Examiner* — Craig D Ricci
(74) *Attorney, Agent, or Firm* — Stinson LLP

(57) ABSTRACT

External compositions containing one or more lipophilic naphthoic acid retinoid compounds are described. The external compositions are applied to skin where they stimulate skin repair and visibly improve skin damage caused by photoaging and acne.

20 Claims, No Drawings

LIPOPHILIC THIRD GENERATION RETINOID

CROSS-REFERENCE TO RELATED APPLICATIONS

This application claims priority to U.S. Provisional Application No. 63/134,772 filed Jan. 7, 2021, which is hereby incorporated by reference in its entirety.

FIELD OF THE INVENTION

The present invention relates to various external compositions containing one or more lipophilic naphthoic acid retinoid compounds, methods of using these compositions, and processes for preparing these compositions. The external compositions are applied to skin where they stimulate skin repair and visibly improve skin damage caused by photoaging and acne.

BACKGROUND OF THE INVENTION

Visible skin damage, particularly on the face, is one of the most common targets of dermatological and cosmetic treatments. Untreated facial skin damage may cause anxiety and psycho-emotional trauma. Facial skin damage is often caused by photoaging, and may present itself as actinic keratosis, solar lentigines, loss of underlying skin collagen, loss of elastin, wrinkles and sagging skin. At an early stage, photoaging may present as inflamed erythema as well as enlarged freckles. Other facial skin damage may be caused by acne, resulting in both inflamed pores and post-acne scarring.

Topical retinoids are the first line treatment for skin damage cause by photoaging and acne in both cosmetic and prescription drug products. These include first generation retinoids that are related to Vitamin A, such as retinol (retinyl alcohol) and retinoic acid. Furthermore, there second generation retinoids that are further variations of Vitamin A. These materials are all lipophilic and relatively easy to formulate in topical products, though they suffer from two principal drawbacks: they cause significant erythema, scaling and peeling of skin, and they are teratogenic.

Third generation retinoids, such as adapalene (6-(3-(1-adamantyl)-4-methoxyphenyl)-2-naphthoic acid) are retinoids of the naphthoic acid type without any Vitamin A characteristics. They have proven to be just as effective for treating acne and photodamaged skin, but with less irritancy and less risk of teratogenicity than first and second generation retinoids.

Adapalene is free carboxylic acid and is in a solid crystalline form. It is not oil or water soluble. Ethanol is the only known solvent for adapalene. This creates major commercial and scientific challenges for delivering topical adapalene to the skin, because ethanol is an undesirable solvent in skincare due to its damaging effects on the skin barrier and skin biome. Significant research has been conducted to identify topical formulations that permit adapalene to remain suspended or sufficiently dispersed in an aqueous phase of a topical product without the use of ethanol. Water-based adapalene formulations have been developed that employ glycols such as propylene glycols, along with dispersing surfactants such as those derived from polyethylene glycol (PEGs), and associative gelling agents that can thicken or gel water such as carbomer. Examples of a such inventive formulas for including adapalene in water-based formulas can be found these patents: U.S. Pat. No. 8,716,341B2, U.S. Ser. No. 10/702,466B2, U.S. Pat. No. 9,271,930B2, and U.S. Pat. No. 8,404,220B2.

Despite the success of creating water-based delivery of adapalene, there has been no success incorporated adapalene into an oil phase. This has limited the utility of third generation retinoids, because unlike first generation retinoids, they cannot be compounded into anhydrous oils, ointments, balms, or high oil content barrier creams. Since adapalene cannot be formulated into such products, it cannot benefit from the penetration enhancing and healing effects that oil-based delivery vehicles provide. Thus, there remains a need for new strategies that can provide for delivery of the adapalene active component with oil-based ingredients.

The present disclosure relates to adapalene esters that are lipophilic and can be delivered in an oil phase, providing an advantage over adapalene, which is insoluble in oil or water and sparingly soluble in ethanol. Adapalene esters have the additional advantage of the ability to provide the adapalene ester active compound already predissolved in an oil carrier (i.e., as a premix), which is more convenient for sale and transportation and easier for a cosmetic manufacturer to use. While pure adapalene could be predissolved in ethanol, ethanol is a controlled substance and flammable, making such a premix impractical.

SUMMARY OF THE INVENTION

In various aspects, the present invention relates to anti-photoaging and anti-acne active compounds of Formula I:

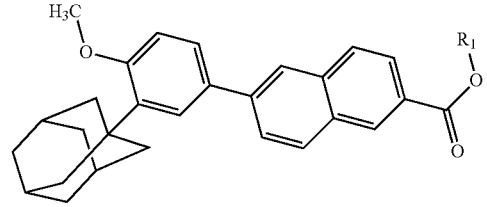

Formula I wherein $R_1$ is substituted or unsubstituted hydrocarbyl having six to twenty-two carbon atoms.

Further aspects relate to topical skin care compositions comprising an ester of adapalene (e.g., a compound of Formula I) in a cosmetically acceptable carrier.

Still further aspects relate to an ester or diester of adapalene that is soluble in a lipophilic carrier.

DETAILED DESCRIPTION OF THE INVENTION

In general, the present invention relates to various external compositions containing one or more lipophilic naphthoic acid retinoid compounds, methods of using these compositions, and processes for preparing these compositions. The external compositions are applied to skin where they stimulate skin repair and visibly improve skin damage caused by photoaging and acne.

Various lipophilic derivatives of adapalene that have a high solubility in cosmetic oils and emollients have been discovered. The lipophilic adapalene derivatives when topically applied provide the benefits of adapalene, yet can be compounded directly in an oil phase of a cosmetic or pharmaceutical formulation, and avoid entirely the need for technologies to disperse adapalene into a water phase. The lipophilic adapalene derivatives can be used in formulations that are free from ethanol, glycols, or polyethylene glycol. The lipophilic adapalene derivatives can be formulated into high oil content formulas that provide for improved barrier protection as compared to water-dispersed adapalene formulas.

Accordingly, the present invention provides for active agents that are lipophilic adapalene derivatives that can be used for treating acne and photoaging. These third generation retinoids include esters of adapalene with $C_6$-$C_{22}$ alcohols. For example, the esters of adapalene include those of Formula I:

Formula I

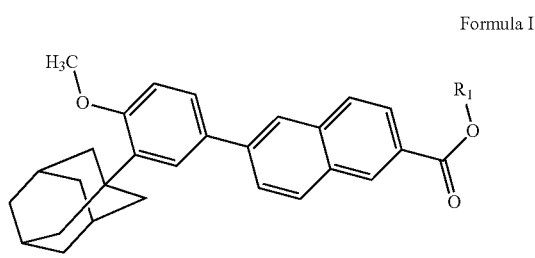

wherein $R_1$ is substituted or unsubstituted hydrocarbyl having six to twenty-two carbon atoms. The hydrocarbyl can be branched or linear, saturated or unsaturated. In various embodiments, $R_1$ a saturated or unsaturated, linear or branched, aliphatic hydrocarbyl group. Preferably, $R_1$ is a substituted or unsubstituted branched or linear alkyl or alkenyl having 6 or more carbon atoms, such as $C_6$-$C_{22}$, $C_6$-$C_{18}$, $C_8$-$C_{16}$, or $C_{12}$-$C_{14}$ carbon chain. When $R_1$ is alkenyl, the substituent has at least one double bond, but can optionally have two or more double bonds. Examples of acceptable hydrocarbyl groups ($R_1$) include $C_6$-$C_{22}$ alkyl or alkenyl groups. Among them $C_8$, $C_{12}$ and $C_{16}$ alkyl, C18-1 alkenyl, and C22-1 alkenyl are preferable. Diesters of Formula I are also envisioned in which $R_1$ is derived from a diol and is substituted or unsubstituted hydrocarbyl as described above having three, four, five, six or more carbon atoms. The alkyl ester chain or diester chain is preferably one that that is soluble in an oil phase and is mutually soluble with lipophilic emollients typically used in topical skin products. The adapalene esters may be in the form of an amorphous solid (i.e. non-crystalline solid).

In one preferred embodiment, $R_1$ is an oleyl group (also referred to as C18-1), a $C_{18}$ linear alkenyl according to Formula II:

Formula II

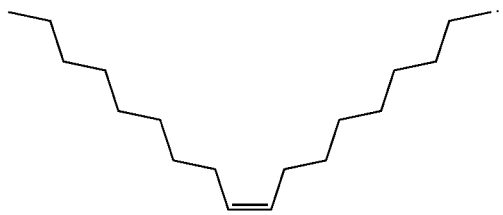

In another preferred embodiment, $R_1$ is an erucyl group (also referred to as C22-1), a $C_{22}$ linear alkenyl according to Formula III:

Formula III

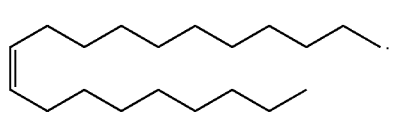

Esterification of the adapalene can be accomplished by the following process. The adapalene, which is a carboxylic acid, can be added in stoichiometric quantities to the long chain alcohol in a solvent. The choice of solvent can include using excess of the long chain alcohol. Esterification catalysts, such as sulfonic acids, organo-tin, or organic-titanium catalysts can be used to increase the rate of reaction, while the water of reaction can be removed by a reflux condenser. Downstream purification by column chromatography, distillation, solvent washing, and re-crystallization may be used to further purify the adapalene ester compound.

One preferred method of producing adapalene esters is via transesterification, with the starting material being methyl adapalate, the methyl ester of adapalene. This process is similar to the esterification process described above. However, the transesterification releases methanol, as opposed to water, and methanol is removed from reaction by evaporation. The long chain alcohol replaces the methanol in the ester group.

Diesters of adapalene can be similarly prepared by reacting one mole of a diol with two moles of adapalene. Examples of suitable diols include propylene glycol, butylene glycol and neopentyl glycol.

The present invention also comprises solutions of the active agent in cosmetically acceptable oils and emollients (i.e., lipophilic carriers). These include but are not limited to emollient esters, triglycerides, vegetable oils, polyesters, polyol esters, wax esters such as jojoba oil, guerbet esters, fatty alcohol, vegetable waxes, hydrocarbon fluids such as mineral oils, petrolatum, alkanes and isoalkanes, silicones, and other topical lipophilic emollients known in the art. The lipophilic solutions include the active agent in an amount necessary to achieve anti-photoaging and anti-acne effects. Typically, the adapalene ester is soluble in the lipophilic carrier at a minimum of about 5%, about 6%, about 7%, about 8%, about 9%, about 10% or more by weight. Preferred lipophilic carriers are isoalkanes since they are cosmetically acceptable and very non-polar. Preferred isoalkanes include $C_{12}$-$C_{36}$ isoalkanes, such as isododecane, isohexadecane, hemisqualane, and squalane. The most preferred isoalkane is squalane.

The adapalene ester can be formulated in a premix composition with a non-polar lipophilic carrier at even higher concentrations of the adapalene ester. Typically, the concentration of the adapalene ester in the premix composition will be at least about 10% by weight, and the weight ratio of adapalene ester to lipophilic carrier is from about 1:9 to about 3:7. The premix composition may in the form of a homogeneous liquid solution or single phase amorphous solid. For example, as detailed in Example 6, in the case of adapalene C18-1 ester dissolved in squalane, we have found that at 20% levels, the premix forms a homogenous amorphous solid.

The present invention further comprises other external compositions containing the active agent dissolved or dispersed in oils and emollients, typically referred to as an oil phase, where the oil phase is further dispersed in a physiologically acceptable topical formulation, such as water-in-oil or oil-in-water emulsion, or a suspension of oil droplets within aqueous matrix such as a gel.

In addition, the present invention further relates to external compositions containing a lipophilic adapalene ester to inhibit or eliminate signs of photoaging and acne, such as reducing aging spots, discoloration spots, redness, blemishes, fine lines, and wrinkles. Said external compositions are particularly distinct because they contain a lipophilic third generation naphthoic acid retinoid, which can incorporate into skin lipids with greater easy that non-lipophilic adapalene. Typically, the lipophilic adapalene ester active agent is present in such external compositions at a concentration of from about 0.1% to about 2% by weight and can be readily formulated from the premix composition described above by mixing the premix composition with other cosmetically acceptable ingredients.

The lipophilic adapalene ester herein may be combined in an external composition with other ingredients intended to inhibit photoaging and acne, or to reduce aging spots, discoloration spots, redness, blemishes, fine lines, and wrinkles. Examples of said ingredients include, but are not restricted to ascorbic acid and derivatives thereof, ferulic acid, azelaic acid, kojic acid, mandelic acid, alpha-hydroxy acids, beta-hydroxy acids, lipohydroxyacids, fruit acids, gluconolactone, heparan sulfate, arbutin, niacinamide, resveratrol, hydroquinone, exfoliants, keratolytics, plant extracts, marine extracts, ferment extracts, isoflavones, bisabolol, anti-aging peptides, retinol, retinoic acid, retinyl esters, retinoic acid esters, and other retinoids.

EXAMPLES

The following non-limiting examples are provided to further illustrate the present invention.

Example 1—Synthesis of Lauryl Adapalene Ester Active Agent

The starting materials, methyl adapalene and $C_{12}$ alcohol (lauryl alcohol) were combined and transesterified as described herein. $C_{12}$ alcohol was added in excess of stoichiometric quantity. Material was heated to between 90-100° C., and the reaction proceeded until all methanol was removed by evaporation. The resulting reaction mass was purified by silica gel column chromatography to yield the pure lauryl adapalene ester active agent (lauryl adapalene).

Example 2—Synthesis of Adapalene Oleyl Ester Active Agent

The starting materials, methyl adapalene and C18-1 alcohol (oleyl alcohol) were combined and transesterified as described herein. C18-1 alcohol was added in excess of stoichiometric quantity. Material was heated to between 90-100° C., and the reaction proceeded until all methanol was removed by evaporation. The resulting reaction mass was purified by silica gel column chromatography to yield the pure adapalene oleyl ester active agent (adapalene C18-1 or oleyl adapalene).

Example 3—Anhydrous External Composition

Approximately 5 grams of lauryl adapalene solids were dissolved in 95 grams of liquid MCT oil (caprylic/capric triglyceride), by heating the mixture to 60° C. for fifteen minutes. The 5% wt/wt solution of active agent remained in liquid form for more than one week at room temperature.

Example 4—Micro-Emulsion External Composition

A 5% active solution of oleyl adapalene dissolved in MCT, is mixed with water and emulsifier to form a thin topical skincare emulsion. The concentration of the active agent is 0.5% in the final formulation.

Example 5—Emulsion External Composition

A 5% active solution of capryl adapalene dissolved in MCT, is mixed with additional oils and waxes, and furthermore mixed with water and emulsifier to form a thick topical skincare emulsion. The concentration of the active agent is 0.2% in the final formulation.

Example 6—Properties of Adapalene Oleyl Ester (Also Referred to as Adapalene $C_{18}$-1 or Oleyl Adapalene)

Adapalene oleyl ester is represented by Formula I, when $R_1$ has the structure of Formula II. Formula II is an oleyl group, an eighteen carbon alkenyl with one unsaturated bond. Because of the unsaturated bond in the oleyl group, adapalene oleyl ester is quite polar while also being less crystalline in character, as unsaturated ester chains tend to have more conformational freedom (i.e. flexibility) and tend not to crystallize. Adapalene oleyl ester is an amorphous solid (i.e. non-crystalline solid), so it is soft wax making it easier to dissolve in a lipophilic carrier. As a non-crystalline substance, it does not require high energy (i.e., enthalpy of solution) to dissolve it in a lipophilic liquid.

Example 7—Properties of Adapalene Oleyl Ester in Squalane Premix

Adapalene oleyl ester was dissolved in squalane at a concentration of 20% by weight. Rather than forming a homogenous liquid solution, the premix of adapalene oleyl ester in squalane formed a homogenous amorphous solid. That is, the adapalene oleyl ester did not form a solid that separates from the squalane liquid. Rather, the entire premix mass formed a soft amorphous solid paste. The concentrated 20% adapalene oleyl ester in squalane remains a single homogenous soft solid paste with a melting temperature range of 30-35° C. This is a suitable temperature range for use in the manufacturing of finished cosmetics, which are usually manufactured at 30-80° C. This 20% composition can itself melt when in contact with the skin (33° C.). A combination of adapalene oleyl ester with squalane at high concentration, minimum 20%, provides an advantageous skin beauty treatment that can target acne prone skin with 20% or more adapalene ester, which is not possible with highly insoluble pure adapalene.

The invention claimed is:

1. A compound of Formula I:

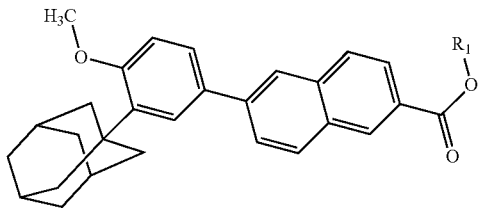

Formula I wherein R₁ is unsubstituted, saturated or unsaturated, linear or branched, aliphatic hydrocarbyl having six to twenty-two carbon atoms.

2. The compound of claim 1, wherein R₁ is unsubstituted linear or branched alkyl or alkenyl.

3. The compound of claim 1, wherein R₁ is C₈, C₁₂, or C₁₆ alkyl.

4. The compound of claim 1, wherein R₁ is a linear eighteen or twenty-two carbon alkenyl.

5. The compound of claim 1, wherein R₁ is an oleyl group according to Formula

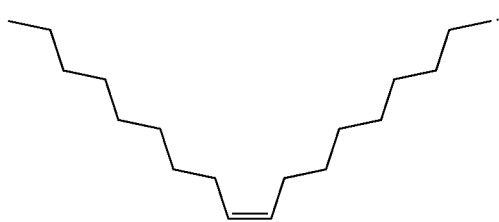

Formula II

6. A topical skin care composition comprising the compound of claim 1 in a cosmetically acceptable lipophilic carrier, wherein the compound is at least partially soluble in the cosmetically acceptable lipophilic carrier.

7. The composition of claim 6, wherein R₁ is an oleyl group according to Formula II:

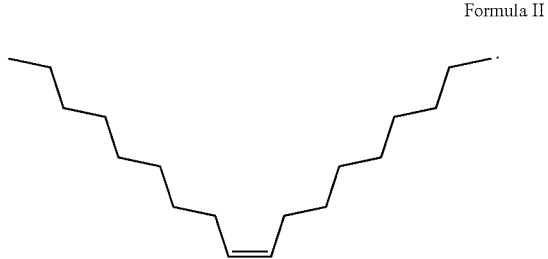 [SMILES: CCCCCCCC/C=C\CCCCCCCC]

Formula II

8. The composition of claim 6, wherein the cosmetically acceptable lipophilic carrier is selected from the group consisting of emollient esters, triglycerides, vegetable oils, polyesters, polyol esters, wax esters, guerbet esters, fatty alcohols, vegetable waxes, hydrocarbon fluids, petrolatum, alkanes, isoalkanes, silicones, and combinations thereof.

9. The composition of claim 6, wherein the cosmetically acceptable lipophilic carrier comprises an isoalkane.

10. The composition of claim 9, wherein the isoalkane is selected from the group consisting of isododecane, isohexadecane, hemisqualane, squalane, and combinations thereof.

11. The composition of claim 9, wherein the isoalkane is squalane.

12. The composition of claim 6, wherein the compound is soluble in the cosmetically acceptable lipophilic carrier at a minimum of about 5% by weight.

13. The composition of claim 6, wherein the weight ratio of the compound to the cosmetically acceptable lipophilic carrier is at least 1:9.

14. The composition of claim 6, wherein the weight ratio of the compound to the cosmetically acceptable lipophilic carrier is from about 1:9 to about 3:7.

15. The composition of claim 6, wherein the composition is a single phase amorphous solid.

16. The composition of claim 15, wherein the composition has a melting temperature range of 30-35° C.

17. The composition of claim 6, wherein the composition further comprises at least one ingredient selected from the group consisting of ascorbic acid and derivatives thereof, ferulic acid, azelaic acid, kojic acid, mandelic acid, alpha-hydroxy acids, beta-hydroxy acids, lipohydroxyacids, fruit acids, gluconolactone, heparan sulfate, arbutin, niacinamide, resveratrol, hydroquinone, exfoliants, keratolytics, plant extracts, marine extracts, ferment extracts, isoflavones, bisabolol, anti-aging peptides, retinol, retinoic acid, retinyl esters, retinoic acid esters, and other retinoids.

18. The composition of claim 6, wherein the composition is free of ethanol and/or glycols.

19. A method of reducing signs of photoaging or acne comprising applying the composition of claim 7 topically to the skin of a subject in need thereof.

20. A method of reducing wrinkles and sagging facial skin comprising applying the composition of claim 7 topically to the facial skin of a subject in need thereof.

* * * * *